(12) United States Patent
Ihde

(10) Patent No.: US 7,775,796 B2
(45) Date of Patent: Aug. 17, 2010

(54) BONE-ADAPTIVE SURFACE STRUCTURE

(75) Inventor: Stefan Ihde, Uetliburg (CH)

(73) Assignee: Biomed Est., Vaduz (LI)

( * ) Notice: Subject to any disclaimer, the term of this patent is extended or adjusted under 35 U.S.C. 154(b) by 1061 days.

(21) Appl. No.: 10/714,200

(22) Filed: Nov. 14, 2003

(65) Prior Publication Data
US 2004/0146835 A1 Jul. 29, 2004

(30) Foreign Application Priority Data
Nov. 15, 2002 (EP) ................... 02090379

(51) Int. Cl.
A61C 8/00 (2006.01)
(52) U.S. Cl. ...................... 433/176; 433/173
(58) Field of Classification Search ......... 433/172–176, 433/220; 623/17.17, 16.11
See application file for complete search history.

(56) References Cited

U.S. PATENT DOCUMENTS

| | | | | |
|---|---|---|---|---|
| 3,683,501 A | * | 8/1972 | Edelman | 433/176 |
| 3,925,892 A | * | 12/1975 | Juillet | 433/176 |
| 4,344,757 A | | 8/1982 | Streel | |
| 4,521,192 A | * | 6/1985 | Linkow | 433/173 |
| 4,522,596 A | | 6/1985 | Ashkinazy | |
| 4,538,304 A | * | 9/1985 | Grafelmann | 433/176 |
| 4,722,687 A | | 2/1988 | Scortecci | |
| 4,768,956 A | * | 9/1988 | Kurpis | 433/173 |
| 4,802,847 A | * | 2/1989 | Komatsu | 433/176 |
| 4,815,974 A | | 3/1989 | Scortecci | |
| 4,842,517 A | * | 6/1989 | Kawahara et al. | 433/173 |
| 4,964,801 A | | 10/1990 | Kawahara et al. | |
| 5,116,226 A | * | 5/1992 | Linkow | 433/176 |
| 5,965,006 A | * | 10/1999 | Baege et al. | 205/666 |
| 6,186,791 B1 | * | 2/2001 | Karmaker et al. | 433/220 |
| 6,238,214 B1 | * | 5/2001 | Robinson | 433/215 |
| 6,277,149 B1 | * | 8/2001 | Boyle et al. | 623/17.16 |
| 6,402,516 B2 | | 6/2002 | Ihde | |
| 6,516,228 B1 | * | 2/2003 | Berrang et al. | 607/57 |
| 2003/0003419 A1 | | 1/2003 | Ihde | |

FOREIGN PATENT DOCUMENTS

| | | |
|---|---|---|
| AT | 392582 | 4/1991 |
| CH | 690416 | 9/2000 |
| DE | 20202424 | 4/2002 |
| EP | 0935949 | 8/1999 |
| FR | 2302715 | 1/1976 |
| WO | WO01/24737 * | 4/2001 |

* cited by examiner

Primary Examiner—Cris L Rodriguez
Assistant Examiner—Yogesh Patel
(74) Attorney, Agent, or Firm—Robert C. Haldiman; Husch Blackwell Sanders LLP

(57) ABSTRACT

The invention concerns bone-adaptive surface structures for lateral jaw implants. Micromechanical and/or macromechanical surface structures having various body forms are incorporated into selected segments of the surface of the base and of the bar that connects the threaded piece with the base to accelerate the healing process after the implant is inserted into the jaw bone and to make a critical improvement in holding the implant firmly in place without rotation.

18 Claims, 3 Drawing Sheets

BONE-ADAPTIVE SURFACE STRUCTURE

CROSS REFERENCE TO RELATED APPLICATIONS

This application claims priority under 35 U.S.C. §119 to EP 02090379.5 filed Nov. 15, 2002, which claims priority to DE 20208975 U filed Jun. 10, 2002.

TECHNICAL FIELD OF THE INVENTION

The invention concerns bone-adaptive surface structures for lateral jaw implants; that is, for implants which are inserted into the jaw from the side, and which are also known as "disk implants."

DESCRIPTION OF THE RELATED ART

Various industrially produced implants have been used for decades in dental implantology. These include cylinder implants, screw implants, leaf implants, and disk implants. Individually produced subperiostal implants also play a part.

These implants developed from a kind of box shape. They generally have a disk-shaped implant base. U.S. Pat. No. 3,925,892 (Juillet) describes an implant with a rectangular base and a post screwed onto it. Then the crown or the prosthesis is fastened to the post. According to U.S. Pat. No. 4,722,687 (Scortecci) a congruent osteotomy instrument was developed later, as well as an osteotomy tool which simultaneously served as its own implant, and so was left in the bone (U.S. Pat. No. 4,815,974). Later, U.S. Pat. No. 4,344,757 described other possible forms, as did U.S. Pat. No. 4,964,801 (Kawahara).

All the developments mentioned above had in common the fact that they essentially improved the geometry, or the external shape, of the implants. That contributed to a broader range of possible uses, lower fracturability, and better retention.

SUMMARY OF THE INVENTION

The strongest possible hold in the jawbone is an essential objective of any implant. Aside from the variously shaped bases intended to help the implant grow into the jaw bone and improve its firm seating, surface structures intended to improve the holding of the implant have been discussed quite recently. These involve combinations of air abrasion ("sandblasting") processes with etching processes. Etching has the additional objective of removing residue from mechanical processing and abrading from the surface of the implant. These processes treat the surface at the microscopic level.

The invention is based on the objective of accelerating the healing process of the implant into the jawbone after its insertion, and of critically improving the anti-rotational retention of the implant.

The objective is attained according to the invention by lateral jaw implants according to the features of Claim 1. Advantageous further developments of the invention appear in Subclaims 2 to 20.

It has been found that significant improvements of the retention of the implant can be achieved by lateral implants, by means of macromechanically acting surface structures and even macromechanical surface forming, independently of the geometry of the implant body. At first glance, it appears impossible to apply macromechanical surface structures to lateral implants. It was determined that the implant bed prepared in the jawbone from laterally must be very thin, so that the blood supply is not too seriously impaired and so that primary bone healing is possible. Surprisingly, it was later found that having a surface structure in the form of grooves with profiles which are corrugated, pointed, or sawtooth-like, and which are arranged in parallel, concentric with the thread carrier, or in the form of a spiral form on the upper and/or the lower surface of the base, and which can at least in part extend onto the bar of the implant, can be inserted relatively easily if the height of the osteotomy slot does not exceed the core height h2 of the surface structure. After insertion of the implant, the surface structures force themselves into the jawbone. This is promoted by the force of chewing, because the surface structures are perpendicular to the masticatory force. That differs from the situation with crestal (screw) implants, in which the threads, etc., lie transversally to the direction of chewing.

It has been determined from histological sections that small particles of bone are scraped off the jawbone during the insertion into the depressions of the surface structures. That avoids formation of voids, and the bone particles that are scraped off substantially accelerate the healing process.

Histologic examinations have also shown that the jawbones optimally tolerate contact of the basal structures of implants having a macromechanical surface structure. If the depth F of the macromechanical surface structure is from 0.05 to 2 µm, direct bone contact with the implant occurs (osseointegration). It is therefore unnecessary to apply an additional microstructure, such as, for example, titanium coatings applied by plasma spraying. Dispensing with such measures not only reduces cost, but also prevents the layers applied from producing supplemental microstructure separating from the surface during insertion of the implant, or later, thus causing inflammation and symptoms resembling polymetallosis.

According to an advantageous further development of the subject of the invention, the surface structures are worked into the base of the implant only in selected annular regions. Such implants present a situation in which only the annular regions with the enlarged surfaces are osseointegrated, while all the other regions experience only moderate osseointegration or are overgrown with connective tissue. This implant configuration is particularly advantageous for use in the vicinity of the maxillary sinuses. In this case the surface of the part of the implant in the vicinity of the maxillary sinus is smooth, resulting in very good self-cleaning, while the cortically anchored regions, i.e., the annular regions, have enlarged surfaces and so are integrated better. In this embodiment, supplemental microstructure of the surfaces by etching, air-abrading, etc., is again not necessarily required with this embodiment of lateral implants.

The advantageous effects noted above also appear if the surface structure consists of bowl-like depressions.

According to a further feature of the invention, the surface structures can be formed by variously shaped depressions and milled-out regions worked into the marginal zones of the base. In this variant embodiment, the geometry of the depressions, which differ from each other, should advantageously be selected such that the forms of the depressions in contact produce a configuration with reentrant angles. Furthermore, the substrate can in turn be formed so that it ends in the peripheral region of the base with a core height of h2.

Aside from the advantages noted which are also attainable with this solution, the peripheral depressions in the base substantially improve the in-growth because the jaw bones tend to close, reaching and filling out the depressions with smaller configurations sooner than those with somewhat larger configurations. In this way, a high initial strength can be attained considerably sooner.

If lateral implants of the type according to the invention also have elastic properties, then the threaded parts sink into the spongy bones under stress. That results in a tension directed centrally on the threaded parts. In this situation, the surfaces of the previously known lateral implants can tear out of the bone combination. However, due to the surface structures according to the invention, it is possible to maintain the combination with the bone even under large stresses. Thus individual implants can be more heavily loaded, with the result that fewer implants per jaw are needed to reproduce the ability to chew. In this way, even severely atrophied jaws can be cared for without bone grafting.

With proper selection of microdimensions and macrodimensions, it is possible to provide an implant which fits biomechanically into the bone but is still easily insertable, and which has a surface structure that offers the implant optimal macromechanical hold in the jawbone. Then the vertically acting masticatory forces are absorbed in an astonishing manner by the likewise vertical structures such as, for example, the grooves made in the surface of the implant base and/or bar.

It is also possible to elevate the surface structure by sintering one or more layers of balls of titanium or a titanium alloy having a diameter of 120 to 220 μm onto the desired surfaces of the implant. This likewise provides higher surface roughness without additional micromechanical measures such as those described above.

From extensive series of histological examinations and cracking tests, it has been found that the best results for adhesion are attained with the dimensions shown below for the bases and surface structures:

Implant diameter D/implant width: 8-15 mm
Height h3 of the implant base where it joints the thread carrier: 0.7-1.2 mm
Distance E between the peaks of the surface structure: 0.2-0.7 mm
Width G of the ring for the implant base: 1.0-2.4 mm
Core height h2: 0.6-0.9 mm
Depth F of the surface structure: 0.05-0.25 mm.

Lathe-turning or milling processes, or a combination of those two processes, are particularly suitable for producing implants according to the invention. The well-known air-abrading or etching processes are used advantageously for final working.

The surface structures according to the invention can be produced in a particularly elegant manner using ablative laser processes. This kind of production also favors production of bowl-like surface structures.

BRIEF DESCRIPTION OF THE DRAWINGS

Reference is now made more particularly to the drawings which illustrate the best presently known mode of carrying out the invention and wherein similar reference characters indicate the same parts throughout the views.

DETAILED DESCRIPTION

Figure 1A:
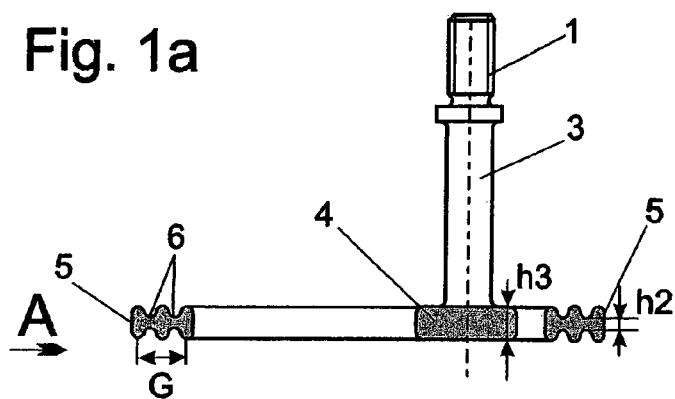
FIG. 1a is Section L-L of FIG. 1b.

As can be seen in FIG. 1, 1 indicates the screw thread that connects with the prosthesis. That thread can be made as an internal or external thread. Numeral 2 indicates the annular body of the implant. Numeral 3 is the thread holder which connects the annular body with the threads. The bar that connects the thread holder 3 to the base 2 is designated as 4. It has been determined that implants of this type transfer the masticatory force essentially into the peripheral annular section of the base 2, indicated here by 5, which is anchored in the cortical jaw bone. Numbers 6a, 6b and 6c indicate the surface structure according to the invention that extends beyond the level of the base 2. G indicates the width of the base 2 or the diameter of the base 8.

Figure 1B:
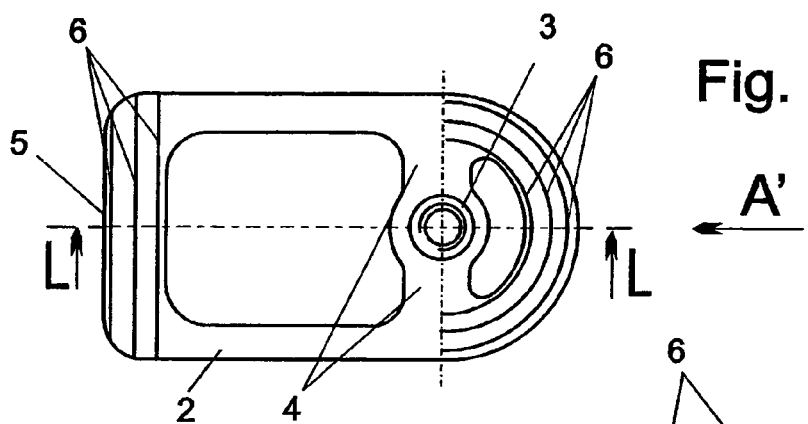
FIG. 1b is a plan view of a bone-adaptive lateral jaw implant with surface structures according to the invention, with a rectangular base.

As shown in FIG. 1b, the surface structures according to the invention are formed by grooves 6 which can run parallel with each other, as shown at the left of the thread holder 3, or concentrically, as shown at the right of the thread holder 3.

Figure 1C:
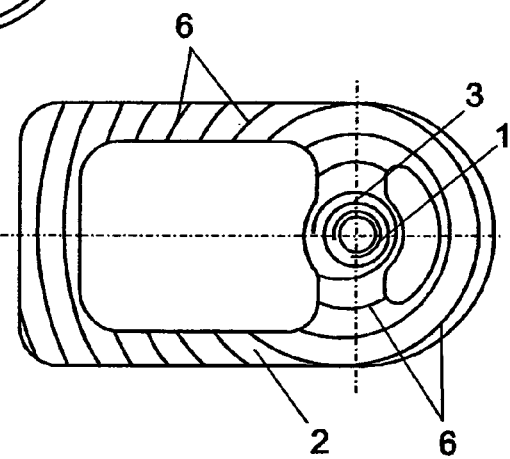
FIG. 1c is a plan view of a jaw implant according to the invention with a spiral design and arrangement of the surface structures. This design can be held extraordinarily well (strongly) in the bone.
Figure 4:
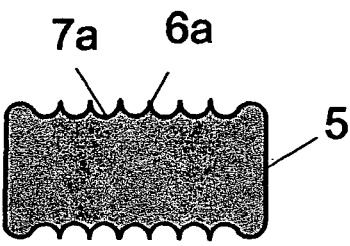
FIG. 4 is a sectional view of an annular section of the base with a surface structure ending in points.
Figure 5:
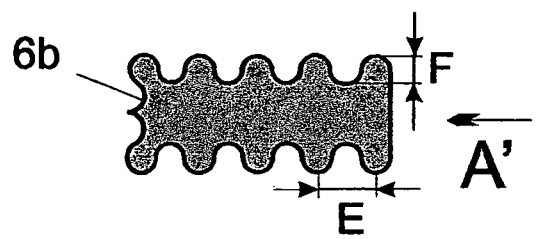
FIG. 5 is an annular section of a base with a corrugated surface structure, with a pointed surface structure also provided in the inner wall area of the base.
Figure 7:
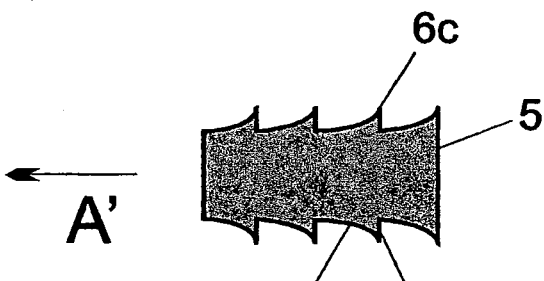
FIG. 7 is an annular section of a base with a sawtooth-like surface structure.

In the embodiment shown in FIG. 1c, the surface structures 6, which can have a profile such as shown in FIGS. 4, 5 and 7, have a spiral shape and extend essentially over the entire upper and/or lower surface of the base 2, with the center of the spiral placed in the region where the screw holder 3 connects to the foot 4.

Figure 2:
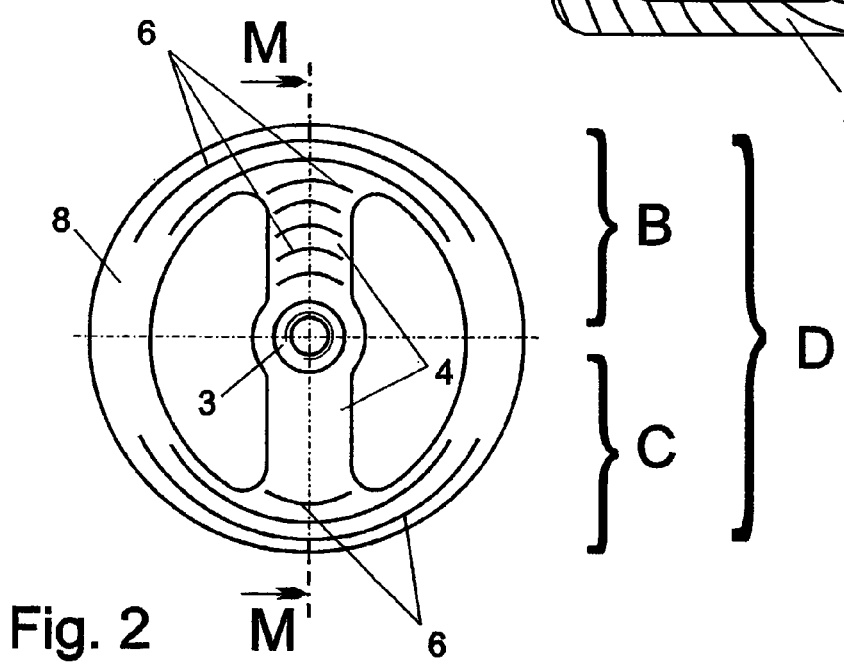
FIG. 2 is a lateral jaw implant according to the invention with a round base.

FIG. 2 shows another variant of the basic form of the implant, a round implant in this case. The corrugated or pointed surface structures 6a, 6c, which are formed by the grooves 6, are placed as far as the thread holder 3 in the upper part B of FIG. 2, while in the lower part C of FIG. 2 they extend only to the junction of bar 4 with the base 8. The latter of the two embodiments has the advantage that this design increases the breaking strength of the base 2 in the vicinity of the bar 4. D indicates the implant diameter. There is a single diameter for the round implants, while there can be numerous diameters for longitudinal implants or for implant with multiple force-transferring bases.

Figure 3:
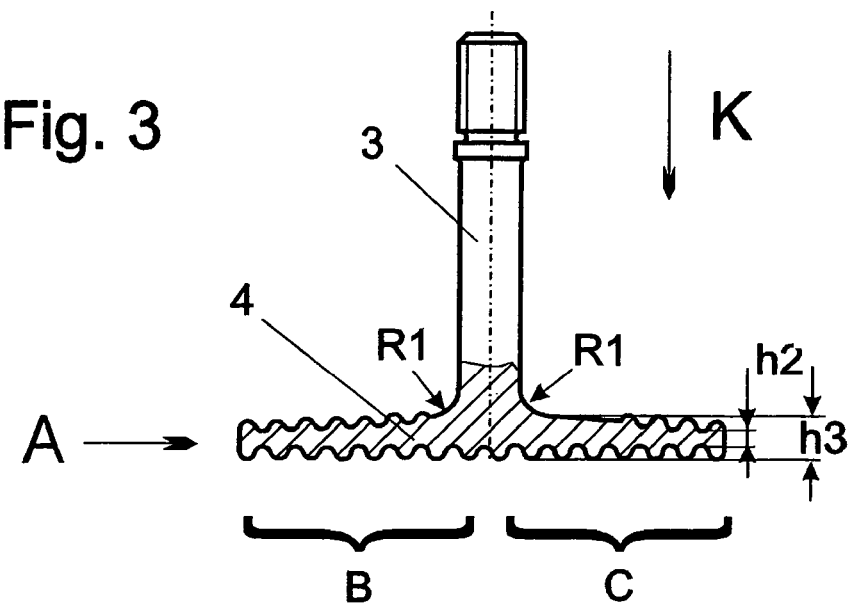
FIG. 3 is the section M-M through the bar of the implant shown in FIG. 2 with a further advantageous arrangement of a surface structure according to the invention.

In the presentation of FIG. 3, the surface structures continue up to the screw holder 3 at the left part (B) of the figure, while in the right part (C) they terminate at the left. Therefore, the central height h3 of the base 8 terminates at a core height h2 of the ring of the base 8, so that the surface structures according to the invention either maintain the central height h3 or, as shown in the right part, C, diminish outwardly and are less high in the peripheral region of the base 2, resulting in a core height h2. It is entirely possible, though, for the surface structure in the peripheral region to have a height which exceeds the central height H3 of the base 8, 2 and the surface structure terminates in the vicinity of the junction of the thread holder 3 and foot 4 at the implant height h3 with continuous decrease of the depth of the selected profile shape.

R1 indicates the radius of the transition from the thread holder 3 to the bar 4. K indicates the direction of the principal masticatory force. However, forces that occur with laterotrusion motions during the act of chewing also act at an angle, even perpendicularly, to the main masticatory force.

FIG. 4 shows a bone-adaptive surface structure with a corrugated profile which terminates in points, with which the substrate or the wave valleys 7a have essentially a round concave shape.

FIG. 5 shows another optimized variant for the shaping of the surface structure 6b which is also inserted in the vertical sidewall surface of the force-transferring base, 2, 8. The shaping of such structures on the outer side of the implant in particular is being proven clinically. A' indicates the direction opposite to the insertion path. E indicates the distance between corrugations or points of the surface structure. According to the results of the investigations on which this application is based, it is optimally 0.2-0.7 mm.

Figure 6:
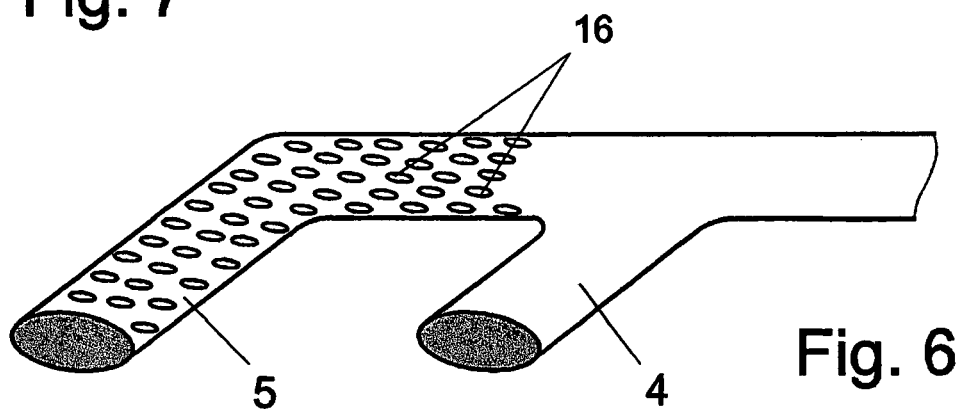
FIG. 6 is a view of a base with a bowl-like surface structure.

FIG. 6 shows a section of the base in which the surface structure according to the invention is formed by individual elevations with bowl-like depressions between them made by milling or by lasers. The depth of these depressions is preferably 0.05-0.25 mm, as was determined, surprisingly, by investigations. Greater depths retard osseointegration, while lesser depths do not give good results for bone adherence of the implant.

Surface structures with edges 10 perpendicular or approximately perpendicular to the direction of insertion and slowly diminishing concave sides 11 also give particularly good adhesion values. These sawtooth-like structures can be produced either just over the annular region of the base or over the entire implant. However, for reasons of production technology, it can be difficult to provide truly perpendicular edges because the initially vertical edges formed by lathe-turning or machining can be flattened by ablative abrading. In production, the result is that the angles are between 80 and 90 degrees, but they all give good clinical results.

Figure 8:
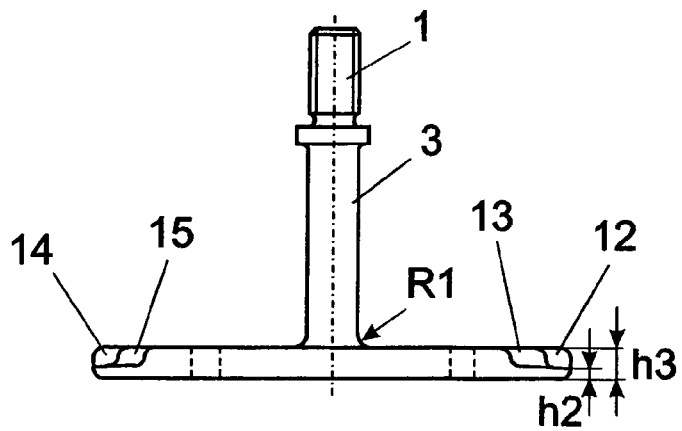
FIG. 8 is a front view of the implant shown in FIG. 9.
Figure 9:
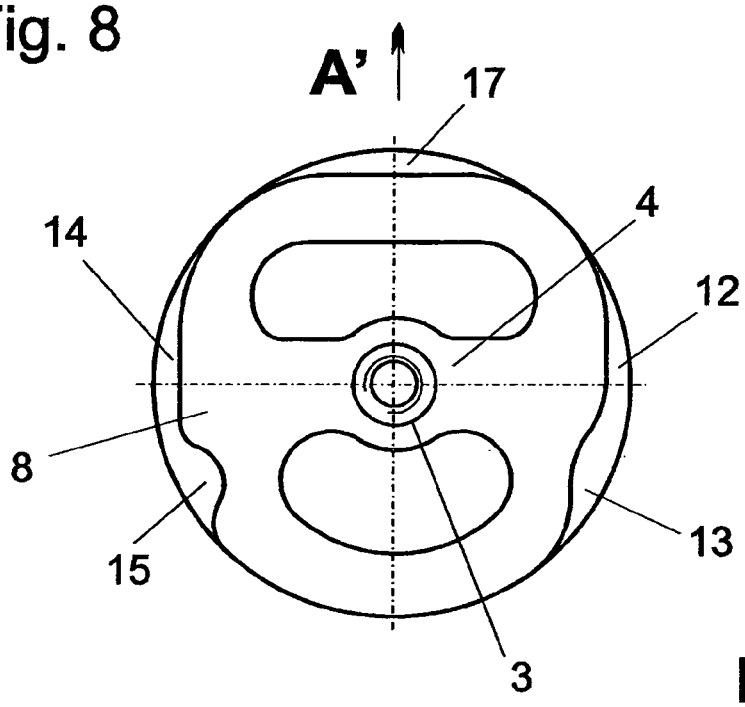
FIG. 9 is a lateral implant having depressions worked into its base, in agreement with the present invention.
Figure 10:
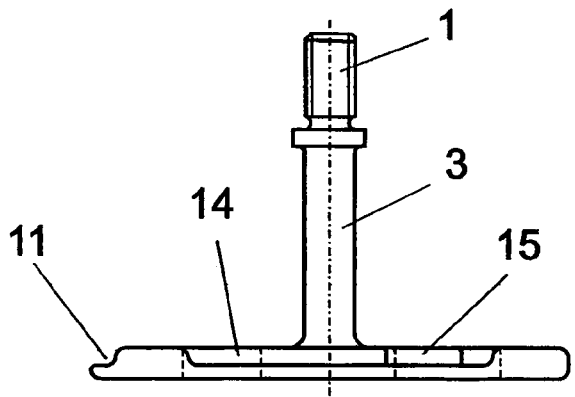
FIG. 10 is the left side view of the implant shown in FIG. 9.

In the embodiment shown in FIGS. 8 to 10, depressions 12, 13 and 14, 15 are made in the base 8 of the lateral implant. They have a different configuration, in that the geometries that deviate from each other are selected so that there is a reentrant angle between the forms of the adjacent depressions 12, 13 and 14, 15. Following insertion of the implant into the ground osteotomy slot, the jaw bone, which has the tendency to draw together, will reach into the lesser depressions 12 and 14 more quickly than into the depressions 13, 15 with the greater shaping. In this way, high initial strength is attained relatively rapidly, with the bone particles scraped off during the insertion and collected in the depressions 13, 15 promoting bone formation and healing of the implant. The depression 17, directed toward the underside of the implant and preferably placed obliquely, makes it easier to insert the implant into the osteotomy slot.

What is claimed is:

1. An osteal implant comprising:
   a shaft, said shaft having a longitudinal axis and having a first end and a second end at opposing ends of said longitudinal axis;
   said first end having a mount for a device to be implanted;
   said second end being attached to a top surface of a base;
   said base being substantially orthogonal to said longitudinal axis in at least two non-parallel directions, said base being substantially planar; at least one of a top surface or a bottom surface of said base having a first height at a first radial distance from said longitudinal axis and a second height at a second radial distance from said longitudinal axis;
   said first height being maintained through at least two directions radial to said longitudinal axis;
   said second height being maintained through at least two directions radial to said longitudinal axis, and
   both of said top surface and said bottom surface being disposed for osseo integration.

2. The implant of claim 1 wherein said first height is maintained through an arc between said at least two directions radial to said longitudinal axis.

3. The implant of claim 1 wherein said first height and second height alternate periodically.

4. The implant of claim 1 wherein said first height and second height alternate, said alternation comprising corrugation.

5. The implant of claim 1 wherein at least one of said heights has a sharp edge.

6. The implant of claim 1 further comprising a third height, said third height being a different radial distance from said longitudinal axis than either said first height or said second height.

7. The implant of claim 1 wherein at least one of said heights varies in said radial direction to comprise a spiral.

8. The implant of claim 1 wherein at least one of said heights comprises a plurality of bowl like depressions.

9. The implant of claim 1 wherein said heights vary in a range from about 0.05 millimeters to about 0.25 millimeters.

10. The implant of claim 1 wherein said base has an outer perimeter and said outer perimeter includes at least three substantially straight edges.

11. The implant of claim 1 wherein said first and second height comprise barbs oriented to resist extraction of said implant in at least one direction.

12. The implant of claim 1 wherein said at least one of said heights comprises ridges, said ridges being curvilinear on a first side of said base and concave to a first direction and said ridges being substantially rectilinear on a base side substantially opposite from said first side.

13. The implant of claim 1 wherein at least one of said first height or said second height repeat and vary in extent radially.

14. The implant of claim 1 wherein said second height is at a marginal zone of said base, said marginal zone being substantially along a height of a periphery of said base.

15. The implant of claim 14 wherein said marginal zone varies in radial distance from said longitudinal axis.

16. The implant of claim 14 wherein said marginal zone comprises reentrant angles.

17. The implant of claim 1 wherein both said first height and said second height are maintained through an arc between at least two directions radial to said longitudinal axis.

18. The implant of claim 17 wherein said arc is substantially 180°.

* * * * *